US009579637B2

(12) United States Patent
Xu et al.

(10) Patent No.: US 9,579,637 B2
(45) Date of Patent: Feb. 28, 2017

(54) SAPO-34 MOLECULAR SIEVE HAVING BOTH MICROPORES AND MESOPORES AND SYNTHESIS METHODS THEREOF

(71) Applicant: Dalian Institute of Chemical Physics, Chinese Academy of Sciences, Dalian (CN)

(72) Inventors: Lei Xu, Dalian (CN); Peng Tian, Dalian (CN); Zhongmin Liu, Dalian (CN); Lixin Yang, Dalian (CN); Shuanghe Meng, Dalian (CN); Changqing He, Dalian (CN); Cuiyu Yuan, Dalian (CN); Yue Qi, Dalian (CN)

(73) Assignee: Dalian Institute of Chemical Physics, Chinese Academy of Sciences, Dalian (CN)

( * ) Notice: Subject to any disclaimer, the term of this patent is extended or adjusted under 35 U.S.C. 154(b) by 648 days.

(21) Appl. No.: 13/924,462

(22) Filed: Jun. 21, 2013

(65) Prior Publication Data

US 2013/0287680 A1    Oct. 31, 2013

Related U.S. Application Data

(62) Division of application No. 12/302,728, filed as application No. PCT/CN2007/002348 on Aug. 6, 2007, now abandoned.

(51) Int. Cl.
| | | |
|---|---|---|
| *B01J 29/06* | (2006.01) | |
| *B01J 27/182* | (2006.01) | |
| *B01J 29/85* | (2006.01) | |
| *B01J 29/04* | (2006.01) | |
| *C01B 39/04* | (2006.01) | |
| *C01B 39/10* | (2006.01) | |
| *C01B 39/54* | (2006.01) | |
| *B01J 37/00* | (2006.01) | |
| *C01B 37/08* | (2006.01) | |
| *C07C 1/20* | (2006.01) | |
| *C10G 3/00* | (2006.01) | |
| *B01J 35/10* | (2006.01) | |

(52) U.S. Cl.
CPC ............ *B01J 29/85* (2013.01); *B01J 29/041* (2013.01); *B01J 35/1061* (2013.01); *B01J 37/0018* (2013.01); *C01B 37/08* (2013.01); *C01B 39/04* (2013.01); *C01B 39/10* (2013.01); *C01B 39/54* (2013.01); *C07C 1/20* (2013.01); *C10G 3/49* (2013.01); *B01J 35/10* (2013.01); *B01J 35/109* (2013.01); *B01J 35/1057* (2013.01); *C10G 2400/20* (2013.01); *Y02P 30/20* (2015.11)

(58) Field of Classification Search
USPC .................... 502/60, 214; 423/705
See application file for complete search history.

(56) References Cited

U.S. PATENT DOCUMENTS

| 4,440,871 A  * | 4/1984 | Lok .......................... B01J 20/18 208/114 |
| 6,565,826 B2 * | 5/2003 | Jacobsen ................ B01J 29/041 423/705 |
| 2003/0120117 A1 | 6/2003 | Hidaka et al. |
| 2006/0107830 A1 | 5/2006 | Miller et al. |
| 2010/0081564 A1 | 4/2010 | Voskoboynikov et al. |

FOREIGN PATENT DOCUMENTS

| CN | 1088483 A | 6/1994 |
| CN | 1106715 A | 8/1995 |
| CN | 1362365 A | 8/2002 |
| JP | 11226391 A | 8/1999 |
| WO | WO 00/06493 | 2/2000 |
| WO | WO 2004/096709 | 11/2004 |

OTHER PUBLICATIONS

Database WPI, Week 200628, Thomson Scientific, London, GB; AN 2006-268004, XP002672459 & JP 2006 089300 A (Nippon Gas Gosei KK) Apr. 6, 2006 (Apr. 6, 2006).
Davis, E. Mark, "Ordered porous materials for emerging applications", Nature, vol. 417, Jun. 2002, pp. 813-821.
Elangovan S. P. et al., "Silicoaluminophosphate Molecular Sieves as a Hydrocarbon Trap," Applied Catalysis B: Environmental, Elsevier, Amsterdam, NL, vol. 57, No. 1, Apr. 15, 2005, pp. 31-36.
Gayubo, Ana G. et al., "Kinetic Modeling of Methanol Transformation into Olefins on a SAPO-4 Catalyst," 2000, Ind. Eng. Chem. Res., 39 pp. 292-300.
He Changqing et al., "Effects of Templates on Properties of SAPO-34 Molecular Sieve," Journal of Fuel Chemistry and Technology, vol. 23, No. 3, Sep. 1995, pp. 306-311.
International Search Report for PCT/CN2007/002348, mailed on Nov. 22, 2007, in 3 pages.
Kloestra, et al., "Overgrowth of mesoporous MCM-41 on faujasite", Microporous Materials, vol. 6, 1996, pp. 287-293.
Supplementary European Search Report issued to corresponding European Patent Application No. EP 07785261, dated Apr. 13, 2012.

(Continued)

*Primary Examiner* — Elizabeth Wood
(74) *Attorney, Agent, or Firm* — Knobbe, Martens, Olson & Bear LLP

(57) ABSTRACT

The present invention relates to a SAPO-34 molecular sieve having both micropores and mesopores and synthesis method thereof. The mesopore diameter in the molecular sieve is in a range of 2-10 nm and the mesopore volume thereof is 0.03-0.3 cm$^3$/g. Triethylamine is used as a template agent and the pore size modifiers are added to the synthesis gel at the same time in the synthesis process, thereby the prepared molecular sieve crystals have mesopore distribution besides micropores. The SAPO-34 molecular sieve synthesized in the present invention can be used as catalysts for conversion of oxygen-containing compounds to lower olefins.

5 Claims, 5 Drawing Sheets

(56) References Cited

OTHER PUBLICATIONS

Tan J. et al., "Crystallization and Si Incorporation Mechanisms of SAPO-34," Microporous and Mesoporous Materials, Elsevier Science Publishing, New York, US, vol. 53, No. 1-3, Jun. 1, 2002, pp. 97-108.

Yuping, et al., "Advances in Synthesis of Micro-Mesoporous Composite Molecular Sieves", *Petrochemical Technology*, vol. 2, 2005, p. 188-194.

* cited by examiner

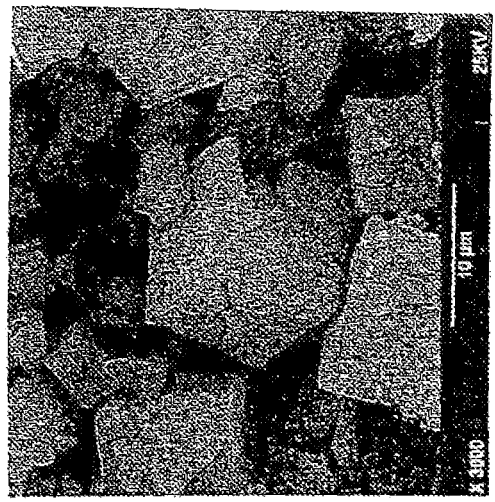
MSP34-2  Fig. 2c
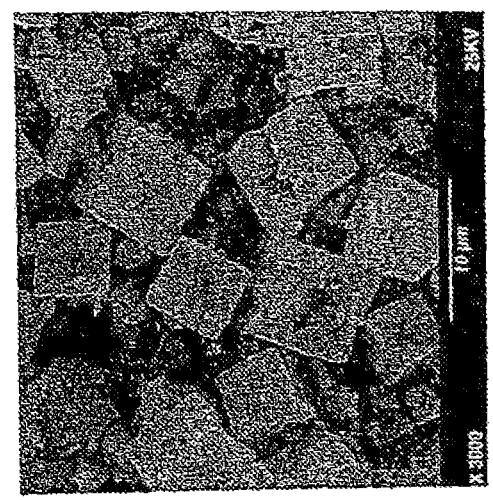
MSP34-1  Fig. 2b
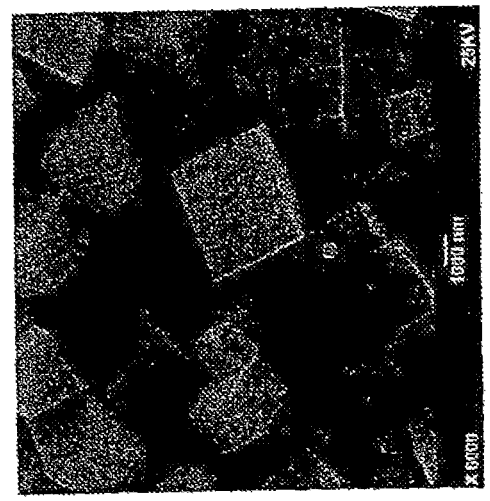
SP34  Fig. 2a

Fig. 2e  MSP34-4
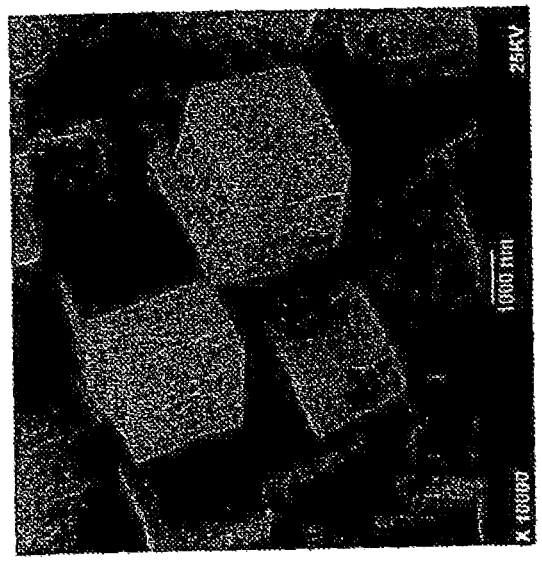
Fig. 2d  MSP34-3

SAPO-34 MOLECULAR SIEVE HAVING BOTH MICROPORES AND MESOPORES AND SYNTHESIS METHODS THEREOF

REFERENCE TO RELATED APPLICATIONS

This application is a divisional of U.S. patent application Ser. No. 12/302,728, filed Nov. 10, 2009, entitled SAPO-34 MOLECULAR SIEVE HAVING BOTH MICROPORES AND MESOPORES AND SYNTHESIS METHOD THEREOF, which is the U.S. National Phase entry of PCT patent application PCT/CN2007/002348, filed Aug. 6, 2007, and which claims priority to Chinese Patent Application No. 200610161073.4, filed Dec. 4, 2006, and to Chinese Patent Application No. 200610089167.5, filed Aug. 8, 2006. The entirety of each of the applications is incorporated herein by reference.

FIELD OF THE INVENTION

The present invention relates to a SAPO-34 molecular sieve having both micropores and mesopores, and the mesopore diameter of the molecular sieve is in a range of 2-10 nm and the pore volume thereof is 0.03-0.3 cm$^3$/g, as well as the synthesis method of the molecular sieve. The molecular sieve prepared by this method is used for the catalysis of the conversion reaction of oxygen-containing compounds to lower olefins.

BACKGROUND

The micropore-mesopore composite molecular sieves having double grade pores of micropores and mesopores have incorporated the pore advantage of mesopore materials with the strong acidic property and the high hydrothermal stability of micropore molecular sieves and made both of the materials complementary and cooperative. Furthermore, the pore diameter and acidic property are both adjustable, that is, a composite material with different pore allocations and acidic property distributions can be prepared by performing an optimized combination of two selected materials with different pore structures and acidic properties. The successful preparation and versatile modes of the molecular sieves with multi-grade pores characterized in assembly will have a wide application perspective in more fields (Nature, 417 (2002) 813).

The synthesis of micropore-mesopore composite molecular sieves began with the preparation of MCM-41/FAU composite material reported by Kloets tra etc. (Micro. Meso. Mater. 6 (1996), 287). Subsequently, numerous researchers devoted to this research field and developed many new composite methods of micropore-mesopore composite molecular sieves. According to the difference of the structure characteristics, the micropore-mesopore composite molecular sieves have two types of composite modes: (1) a composite of two materials of micropore molecular sieve and mesopore molecular sieve. In this type of composite mode, the two materials of micropore molecular sieve and mesopore molecular sieve often show a coating structure, an embedding structure, or a complex combination of both of the structures. Here, an obvious connected interface (transition layer) is present between the two materials and the results characterized by X-ray diffraction (XRD) will show the diffraction peaks corresponding to the two materials, respectively; (2) a composite of mesopores and micropores in a molecular sieve material, and this type of composite mode includes two manners: a micropore molecular sieve with mesopores, that is, a micropore molecular sieve introduced with mesopores, contributes to the diffusion of molecules while maintaining the strong acidic property and stability of the micropore molecular sieve; a mesopore molecular sieve with parts of the properties of micropore molecular sieve, that is, a mesopore material whose amorphous pore walls have been introduced with a primary or secondary structure unit of zeolite, realizes pore walls in a nanometer range. The detailed research progress on this aspect is described in "Petrochemical Technology" (02 (2005) 188). Up till now, all the reported mesopore-micropore composite molecular sieves are of the molecular sieve system consisted of silicon and aluminum, however, as to the molecular sieve system consisted of silicon, phosphorus and aluminum, there are no opened literature reports because the synthesis system is relatively complex.

SAPO-34 molecular sieve was disclosed in U.S. Pat. No. 4,440,871 in 1984. According to the definition of IUPAC on pore diameter size, SAPO-34 belongs to the small pore molecular sieves (<2 nm). SAPO-34 molecular sieve has attracted attention because it has shown superior catalysis performance in the conversion reaction of methanol to olefins (MTO).

DISCLOSURE OF THE INVENTION

An object of the present invention is to provide a SAPO-34 molecular sieve having both micropores and mesopores and the synthesis method thereof. By using the molecular sieve as a catalyst for MTO reaction, the limitation on diffusion mass transfer can be reduced or eliminated, the occurrence of secondary reaction can be decreased, and therefore the catalyst life can be prolonged, as well as the selectivity for ethylene and propylene can be increased.

In order to achieve the object described above, the technical solution of the present invention is to provide a SAPO-34 molecular sieve having both micropores and mesopores, and the mesopore diameter of the molecular sieve is 2-10 nm and the mesopore volume thereof is 0.03-0.3 cm$^3$/g.

According to said SAPO-34 molecular sieve, the surface of the cubic crystal type molecular sieve thereof is rough or broken.

A synthesis method for said SAPO-34 molecular sieve wherein triethylamine is used as a template agent and a pore size modifier is added into a synthesis gel.

Said synthesis method includes the following steps:

a) An initial gel mixture for synthesizing SAPO-34 molecular sieve is formulated;

b) A pore size modifier is added into the initial gel mixture obtained in step a) and stirred sufficiently;

c) The gel mixture obtained in step b) is sealed and heated to crystallization temperature, and a thermostatic crystallization is performed under autogenous pressure; after the crystallization is completed, a solid product is separated, washed to be neutral and dried, and thus as-synthesized SAPO-34 molecular sieve is obtained.

d) The as-synthesized SAPO-34 molecular sieve obtained in step c) is calcined in air to remove the organics contained in the material, and a SAPO-34 molecular sieve having both micropores and mesopores is obtained.

According to said synthesis method, the oxide molar proportions of all components in said initial synthesis gel mixture are:

$SiO_2/Al_2O_3$=0.1~2.0;
$P_2O_5/Al_2O_3$=0.5~15;
$H_2O/Al_2O_3$=10~100;
$TEA/Al_2O_3$=1~5 (TEA is triethylamine);
$T/TEA$=0.01~2 (T is the pore size modifier).

According to said synthesis method, said pore size modifier is one or more selected from the group consisted of aqueous ammonia, tetramethylammonium hydroxide, diethylamine, tripropylamine, di-n-propylamine, n-propylamine, n-butylamine, cyclohexylamine and a mixture thereof.

According to said synthesis method, the crystallization temperature in step c) is 100-250° C., and the preferable crystallization temperature is 160-230° C.

According to said synthesis method, the crystallization time in step c) is 0.5~100 h, and the preferable crystallization time is 2-48 h.

According to said SAPO-34 molecular sieve, it is used as a catalyst for the conversion of oxygen-containing compounds to lower olefins.

By using the SAPO-34 molecular sieve having both micropores and mesopores synthesized in the present invention as the catalyst for MTO reaction, due to the presence of a hierarchical structure, the influence on diffusion mass transfer can be reduced or eliminated, the occurrence of secondary reaction can be decreased, and therefore the catalyst life can be prolonged, as well as the selectivity for ethylene and propylene can be increased, greatly.

DESCRIPTION OF THE DRAWING

FIG. 2: In this figure, FIG. 2a, FIG. 2b, FIG. 2c, FIG. 2d and FIG. 2e are the SEM photos of the samples in example 1, 3, 4, 5 and comparative example 1 of the present invention.

FIG. 3: In this figure.

FIG. 4: In this figure.

DETAILED DESCRIPTION OF THE INVENTION

The present invention is characterized in that the synthesized SAPO-34 molecular sieve has a mesopore pore diameter of 2-10 nm and a mesopore volume of 0.03-0.3 cm³/g.

The present invention is characterized in that the surface of cubic crystals of the synthesized SAPO-34 molecular sieve can be rough or broken.

The present invention is characterized in that triethylamine is used as a template agent and a pore size modifier is added into a synthesis gel.

The present invention provides a synthesis method of a SAPO-34 molecular sieve having both micropores and mesopores, and the preparation process is as follows:

a) An initial gel mixture for synthesizing SAPO-34 molecular sieve is formulated and the oxide molar proportions of all components are:

$SiO_2/Al_2O_3$=0.1~2.0;
$P_2O_5/Al_2O_3$=0.5~15;
$H_2O/Al_2O_3$=10~100;
$TEA/Al_2O_3$=1~5;
T/TEA=0.01-2

The pore size modifier is one or more selected from the group consisted of aqueous ammonia, tetramethylammonium hydroxide, diethylamine, tripropylamine, di-n-propylamine, n-propylamine, n-butylamine, cyclohexylamine and a mixture thereof.

b) The gel mixture obtained in step b) is loaded into a stainless steel autoclave lined with polytetrafluoroethylene inside, sealed and then heated to crystallization temperature, and a thermostatic crystallization is performed under autogenous pressure with a crystallization temperature of 100-250° C. and a crystallization time of 5-100 h. After the crystallization is completed, a solid product is separated by centrifugation, washed to be neutral with deionized water and dried in air at 120° C., and thus as-synthesized SAPO-34 molecular sieve is obtained.

c) The as-synthesized SAPO-34 molecular sieve obtained in step b) is calcined in air to remove the organics and a SAPO-34 molecular sieve with a distribution of micropores and mesopores is obtained.

The present invention was described in detail below by way of examples.

Example 1

Figure 1:
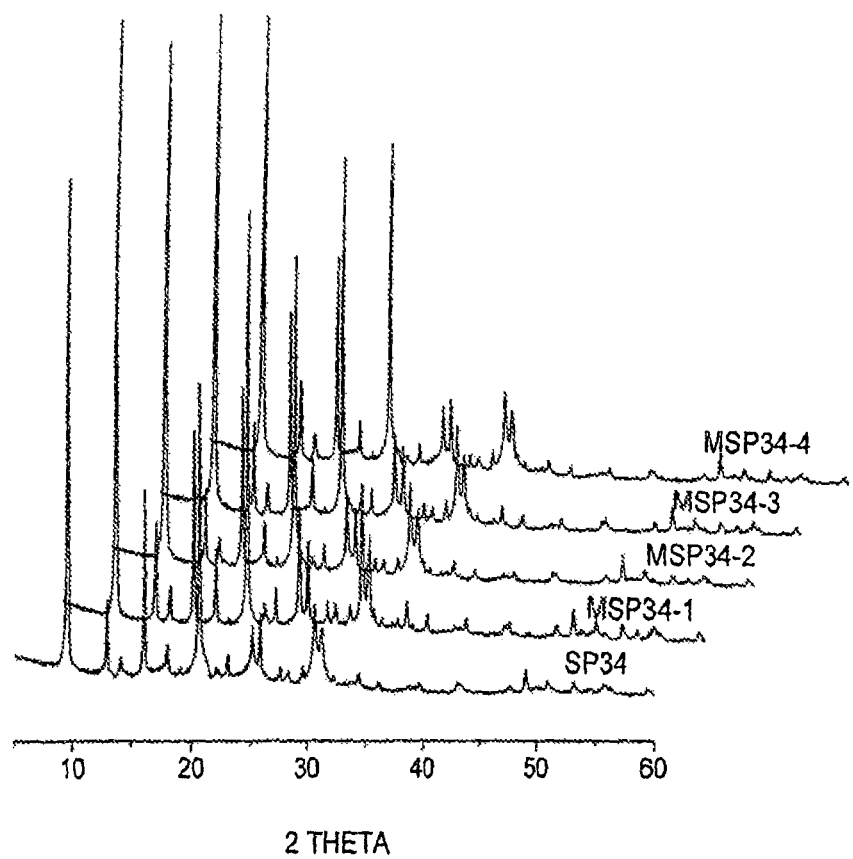
FIG. 1: The XRD spectra of the SAPO-34 synthesized in example 1, 3, 4, 5 added with a pore size modifier and in comparative example 1 without the addition of a pore size modifier.

Gauged raw materials were mixed in a certain sequence in an initial gel molar proportion of 3.0 TEA:0.4 $SiO_2$:$P_2O_5$:$Al_2O_3$:50 $H_2O$:1.0 T (T=n-propylamine), and all the raw materials used were TEA (analytical pure), silica sol ($SiO_2$ content is 30 wt %), pseudobochmite ($Al_2O_3$ content is 70 wt %) and phosphoric acid ($H_3PO_4$ content is 85 wt %). A gel was formed by sufficient stirring, loaded into a stainless steel autoclave lined with polytetrafluoroethylene inside, sealed and heated to 200° C., and under autogenous pressure, a thermostatic crystallization was performed for 12 h. Then a solid product was separated by centrifugation, washed to be neutral with deionized water and dried in air at 120° C., and thus a SAPO-34 molecular sieve was obtained. After calcined the as-synthesized sample at 600° C. for 4 h to remove the template agent, a SAPO-34 molecular sieve having micropores and mesopores was obtained (the number was MSP34-1). The XRD pattern of the as-synthesized sample was shown in FIG. 1 and the SEM photo thereof was shown in FIG. 2. It can be seen that the surface of cubic crystals of MSP34-1 sample was rough or broken.

Comparative Example 1

Gauged raw materials were mixed in a certain sequence in an initial gel molar proportion of 3.0 TEA:0.4 $SiO_2$:$P_2O_5$:$Al_2O_3$:50 $H_2O$, and all the raw materials used were TEA (analytical pure), silica sol ($SiO_2$ content is 30 wt %), pseudobochmite ($Al_2O_3$ content is 70 wt %) and phosphoric acid ($H_3PO_4$ content is 85 wt %). A gel was formed by sufficient stirring, loaded into a stainless steel synthetic kettle lined with polytetrafluoroethylene inside, sealed and heated to 200° C., and under autogenous pressure, a thermostatic crystallization was performed for 12 h. Then a solid product was separated by centrifugation, washed to be neutral with deionized water and dried in air at 120° C., and thus a SAPO-34 molecular sieve was obtained. After calcined the sample at 600° C. for 4 h to remove the template agent, a SAPO-34 molecular sieve was obtained (the number was SP34). The XRD pattern of the sample was shown in FIG. 1 and the SEM photo thereof was shown in FIG. 2. It can be seen that the crystal of MSP34-1 sample presented a cubic type and had a smooth surface.

Example 2

Figures 3A, 3B:
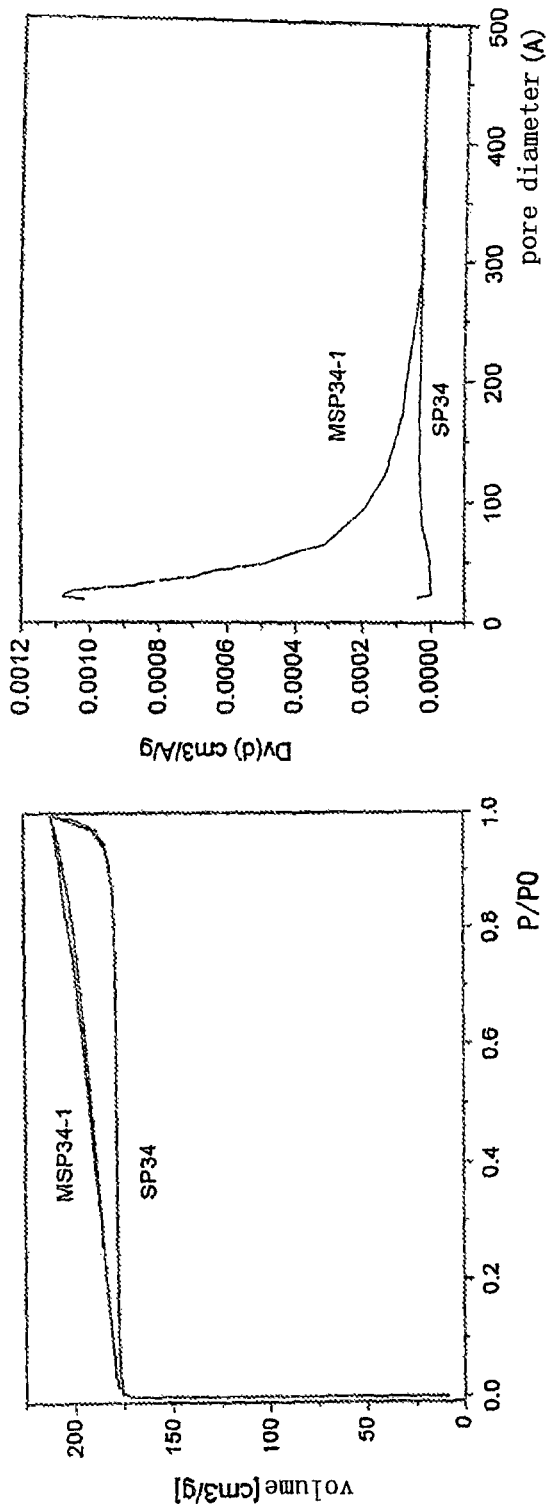
FIG. 3a and FIG. 3b are the schematic diagrams of nitrogen adsorption isotherms and mesopore distributions of the samples with the numbers of MSP34-1 and SP34 in example 2 of the present invention (adsorption line branch, BJH method).

The sample with a number of MSP34-1 obtained in example 1 and the sample with a number of SP34 obtained in comparative example 1 were subjected to a nitrogen physical adsorption characterization to measure the specific surface areas and the pore structures of the molecular sieves. The nitrogen adsorption isotherms and the mesopore distributions were shown in FIG. 3 and the specific surface areas and the pore volumes were shown in Table 1. The results indicated that SP34 sample had very little mesopore structure and the specific surface area and pore volume thereof were substantially produced from the contribution of the micropore parts. MSP34-1 sample had a mesopore distribution with a mesopore pore diameter of 2.3 nm and a mesopore volume of 0.07 cm$^3$/g.

Example 3

Gauged raw materials were mixed in a certain sequence in an initial gel molar proportion of 3.0 TEA:0.4 SiO$_2$:P$_2$O$_5$:Al$_2$O$_3$:50 H$_2$O:0.3 T (T=aqueous ammonia), and all the raw materials used were TEA (analytical pure), silica sol (SiO$_2$ content is 30 wt %), pseudobochmite (Al$_2$O$_3$ content is 70 wt %) and phosphoric acid (H$_3$PO$_4$ content is 85 wt %). A gel was formed by sufficient stirring, loaded into a stainless steel autoclave lined with polytetrafluoroethylene inside, sealed and heated to 200° C., and under autogenous pressure, a thermostatic crystallization was performed for 12 h. Then a solid product was separated by centrifugation, washed to be neutral with deionized water and dried in air at 120° C., and thus a SAPO-34 molecular sieve was obtained. After calcined the sample at 600° C. for 4 h to remove the template agent, a SAPO-34 molecular sieve having micropores and mesopores was obtained (the number was MSP34-2). The XRD pattern of the as-synthesized sample was shown in FIG. 1 and the SEM photo thereof was shown in FIG. 2. It can be seen that the surface of cubic crystals of MSP34-2 sample was rough or broken.

Example 4

Gauged raw materials were mixed in a certain sequence in an initial gel molar proportion of 3.0 TEA:0.4 SiO$_2$:P$_2$O$_5$:Al$_2$O$_3$:50 H$_2$O:1.5 T (T=diethylamine), and all the raw materials used were TEA (analytical pure), silica sol (SiO$_2$ content is 30 wt %), pseudobochmite (Al$_2$O$_3$ content is 70 wt %) and phosphoric acid (H$_3$PO$_4$ content is 85 wt %). A gel was formed by sufficient stirring, loaded into a stainless steel autoclave lined with polytetrafluoroethylene inside, sealed and heated to 200° C., and under autogenous pressure, a thermostatic crystallization was performed for 12 h. Then a solid product was separated by centrifugation, washed to be neutral with deionized water and dried in air at 120° C., and therefore a SAPO-34 molecular sieve was obtained. After calcined the raw power at 600° C. for 4 h to remove the template agent, a SAPO-34 molecular sieve having micropores and mesopores was obtained (the number was MSP34-3). The XRD pattern was shown in FIG. 1 and the SEM photo was shown in FIG. 2. It can be seen that the surface of cubic crystals of MSP34-3 sample was rough.

Example 5

Gauged raw materials were mixed in a certain sequence in an initial gel molar proportion of 3.0 TEA:0.6 SiO$_2$:P$_2$O$_5$:Al$_2$O$_3$:50 H$_2$O 1.6 T (T=tripropylamine+n-propylamine, tripropylamine/n-propylamine=1:1), and all the raw materials used were TEA (analytical pure), silica sol (SiO$_2$ content is 30 wt %), pseudobochmite (Al$_2$O$_3$ content is 70 wt %) and phosphoric acid (H$_3$PO$_4$ content is 85 wt %). A gel was formed by sufficient stirring, loaded into a stainless steel synthetic kettle lined with polytetrafluoroethylene inside, sealed and heated to 200° C., and under autogenous pressure, a thermostatic crystallization was performed for 12 h. Then a solid product was separated by centrifugation, washed to be neutral with deionized water and dried in air at 120° C., and thus a SAPO-34 molecular sieve was obtained. After calcined the raw power at 600° C. for 4 h to remove the template agent, a SAPO-34 molecular sieve having micropores and mesopores was obtained (the number was MSP34-4). The XRD pattern of the as-synthesized sample was shown in FIG. 1 and the SEM photo thereof was shown in FIG. 2. It can be seen that the surface of cubic crystals of MSP34-4 sample was rough or broken.

Example 6

Figure 4B:
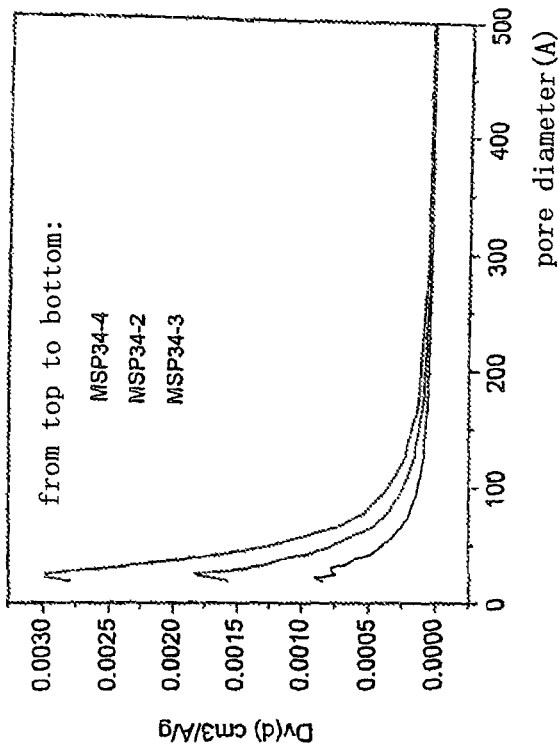
FIG. 4a and FIG. 4b are the schematic diagrams of nitrogen adsorption isotherms and mesopore distributions of the samples with the numbers of MSP34-2, -3 and -4 in example 6 of the present invention (adsorption line branch, BJH method).
Figure 4A:
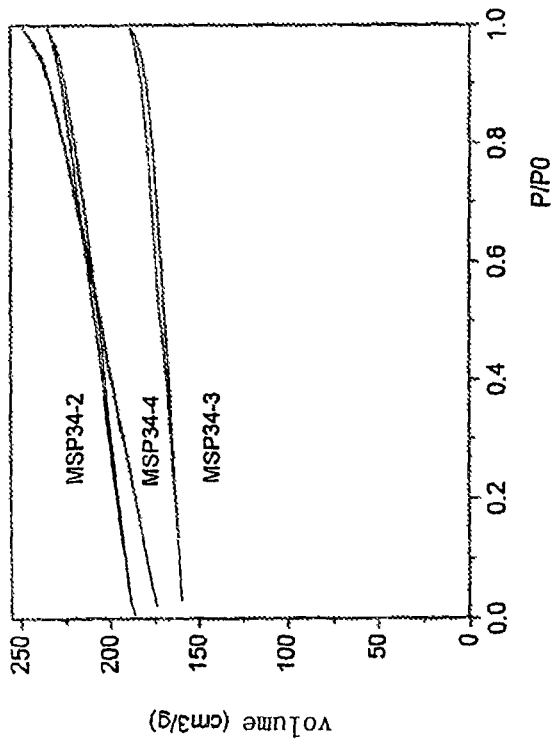

The samples with numbers of MSP34-2, -3 and -4 obtained in example 3, 4 and 5 were subjected to a nitrogen physical adsorption characterization to measure the specific surface areas and the pore structures of the molecular sieves. The nitrogen adsorption isotherms and the mesopore distributions were shown in FIG. 4 and the specific surface areas and the pore volumes were shown in Table 1. The results indicated that the samples MSP34-2, -3 and -4 had a mesopore distribution wherein MSP34-3 sample had two different pore diameters of 2 nm and 3 nm, respectively. The mesopore volumes of the three samples were 0.09, 0.06 and 0.14 cm$^3$/g, respectively.

TABLE 1

The specific surface areas and the pore volumes of the samples

| No. | specific surface area (m$^2$/g) $S_{BET}$ | $S_{micropore}$[a] | micropore volume (cm$^3$/g) | mesopore volume[b] (cm$^3$/g) |
|---|---|---|---|---|
| SP-34 | 530 | 530 | 0.27 | 0.02 |
| MSP34-1 | 584 | 530 | 0.26 | 0.07 |
| MSP34-2 | 656 | 546 | 0.27 | 0.09 |
| MSP34-3 | 518 | 474 | 0.23 | 0.06 |
| MSP34-4 | 603 | 467 | 0.23 | 0.14 |

[a]Calculated using t-plot method
[b]Calculated using BJH method, the cumulative desorption pore volume in a range of 2-50 nm Example 7

The sample with a number of MSP34-1 obtained in example 1 and the sample with a number of SP34 obtained in comparative example 1 were calcined at 600° C. for 4 h under air, then pressed and sieved to a mesh of 20~40. 1.0 g of a sample was weighed and loaded into a fixed bed reactor to carry out a MTO reaction evaluation. The sample was activated at 550° C. for 1 h under nitrogen gas and then reduced to 450° C. to perform a reaction. Methanol was carried by nitrogen gas with a flow rate of 40 ml/min and the weight space rate of methanol was 4.0 h$^{-1}$. The reaction products were analyzed by an on-line gas chromatograph and the results were shown in Table 2.

Example 8

The samples with numbers of MSP34-2, -3 and -4 obtained in example 3, 4 and 5 were calcined at 600° C. for 4 h under air, then pressed and sieved to a mesh of 20~40. 1.0 g of a sample was weighed and loaded into a fixed bed reactor to carry out a MTO reaction evaluation. The sample was activated at 550° C. for 1 h under introducing nitrogen gas and then reduced to 450° C. to perform a reaction. Methanol was carried by nitrogen gas with a flow rate of 40 ml/min and the weight space rate of methanol was 4.0 h$^{-1}$. The reaction products were analyzed by an on-line gas chromatograph and the results were shown in Table 2.

TABLE 2

The reaction results of methanol to olefins over the samples*

| No. | SP34 | MSP34-1 | MSP34-2 | MSP34-3 | MSP34-4 |
|---|---|---|---|---|---|
| CH$_4$ | 2.87 | 2.63 | 2.53 | 2.41 | 2.31 |
| C$_2$H$_4$ | 49.96 | 51.69 | 52.28 | 52.58 | 53.34 |

TABLE 2-continued

The reaction results of methanol to olefins over the samples*

| No. | SP34 | MSP34-1 | MSP34-2 | MSP34-3 | MSP34-4 |
|---|---|---|---|---|---|
| $C_2H_6$ | 0.64 | 0.55 | 0.72 | 0.64 | 0.49 |
| $C_3H_6$ | 34.13 | 34.85 | 33.98 | 33.79 | 34.10 |
| $C_3H_8$ | 0.98 | 0.80 | 0.65 | 0.69 | 0.72 |
| $C_4+$ | 8.57 | 7.56 | 7.85 | 7.76 | 7.94 |
| $C_5+$ | 2.86 | 1.93 | 1.79 | 2.13 | 1.09 |
| $C_6+$ | 0 | 0 | 0.20 | 0 | 0 |
| $\Sigma C_2^= - C_3^=$ | 84.13 | 86.54 | 86.17 | 86.37 | 87.44 |
| Life (min) | 180-200 | 240-260 | 260-280 | 240-260 | 260-280 |

*The highest (ethylene + propylene) selectivity when methanol conversion was 100%.

We claim:

1. A synthesis method for a SAPO-34 molecular sieve, the method comprising:
   a) formulating an initial gel mixture for synthesizing SAPO-34 molecular sieve;
   b) adding a pore size modifier into the initial gel mixture obtained in step a) and stirring;
   c) sealing the gel mixture obtained in step b) and heating the gel mixture obtained in step b) to crystallization temperature, and performing a crystallization step comprising thermostatic crystallization of the gel mixture obtained in step b) under autogenous pressure, and separating a solid product after the crystallization is completed, and washing the solid product to be neutral, and drying the washed solid product, and thus obtaining as-synthesized SAPO-34 molecular sieve; and
   d) calcining the as-synthesized SAPO-34 molecular sieve obtained in step c) in air to remove the organics contained in the material, and obtaining a SAPO-34 molecular sieve having both micropores and mesopores;
   wherein the oxide molar proportions of all components in said initial synthesis gel mixture are:
   $SiO_2/Al_2O_3$=0.1~2.0;
   $P_2O_5/Al_2O_3$=0.5~15;
   TEA/$Al_2O_3$=1~5, wherein TEA is triethylamine;
   T/TEA=0.01~2, wherein T is the pore size modifier;
   said pore size modifier is one or more selected from the group consisting of aqueous ammonia, tetramethylammonium hydroxide, diethylamine, tripropylamine, di-n-propylamine, n-propylamine, n-butylamine, cyclohexylamine and a mixture thereof; and
   the SAPO-34 molecular sieve includes both micropores and mesopores and characterized in that the mesopore diameter of the molecular sieve is 2-10 nm and the mesopore volume thereof is 0.03-0.3 cm³/g.

2. The synthesis method according to claim 1, wherein the crystallization temperature in step c) is 100-250° C.

3. The synthesis method according to claim 1, wherein the crystallization temperature in step c) is 160-230° C.

4. The synthesis method according to claim 1, wherein the crystallization step in step c) comprises a crystallization time of 0.5~100 h.

5. The synthesis method according to claim 1, wherein the crystallization step in step c) comprises a crystallization time of 2-48 h.

* * * * *

UNITED STATES PATENT AND TRADEMARK OFFICE
CERTIFICATE OF CORRECTION

PATENT NO. : 9,579,637 B2
APPLICATION NO. : 13/924462
DATED : February 28, 2017
INVENTOR(S) : Lei Xu It is certified that error appears in the above-identified patent and that said Letters Patent is hereby corrected as shown below:

In Column 3 at Line 67, After "2" insert --.--.

In Column 4 at Line 27, Change "pseudobochmite" to --pseudoboehmite--.

In Column 4 at Line 48, Change "pseudobochmite" to --pseudoboehmite--.

In Column 5 at Line 16, Change "pseudobochmite" to --pseudoboehmite--.

In Column 5 at Line 37, Change "pseudobochmite" to --pseudoboehmite--.

In Column 5 at Line 58, Change "pseudobochmite" to --pseudoboehmite--.

In Column 8 at Line 9 (approx.), In Claim 1, below "$P_2O_5/Al_2O_3=0.5\sim15$;" insert --$H_2O/Al_2O_3=10\sim100$;--.

Signed and Sealed this
Twenty-second Day of May, 2018

Andrei Iancu
*Director of the United States Patent and Trademark Office*